United States Patent

Puckette et al.

Patent Number: 5,840,647
Date of Patent: Nov. 24, 1998

[54] HYDROFORMYLATION PROCESS USING NOVEL PHOSPHITE-METAL CATALYST SYSTEM

[75] Inventors: Thomas Allen Puckette; Ginette Elizabeth Struck, both of Longview, Tex.

[73] Assignee: Eastman Chemical Company, Kingsport, Tenn.

[21] Appl. No.: 929,687

[22] Filed: Sep. 15, 1997

[51] Int. Cl.⁶ ............... B01J 27/188; B01J 27/13; A01N 43/30; C07D 209/82
[52] U.S. Cl. ............... 502/213; 502/230; 514/110; 514/111; 598/440
[58] Field of Search ................... 502/213, 230; 548/440; 514/110, 111

[56] References Cited

U.S. PATENT DOCUMENTS

| | | | |
|---|---|---|---|
| 3,239,566 | 3/1966 | Slaugh et al. | 260/604 |
| 3,527,809 | 9/1970 | Pruett et al. | 260/604 |
| 4,595,753 | 6/1986 | Oswald et al. | 546/21 |
| 4,605,781 | 8/1986 | Tau | 568/454 |
| 4,608,239 | 8/1986 | Devon | 423/210 |
| 4,642,395 | 2/1987 | Hunter et al. | 568/883 |
| 4,871,878 | 10/1989 | Puckette et al. | 568/454 |
| 4,912,155 | 3/1990 | Burton | 524/118 |
| 5,059,710 | 10/1991 | Abatjoglou et al. | 558/78 |

OTHER PUBLICATIONS

Falbe, "New Syntheses with Carbon Monoxide", 1980, Springer–Verlag, p. 73.

Cotton and Wilkinson, "Advanced Inorganic Chemistry", 3rd Edition, 1972, Wiley and Sons, pp. 374–375.

Kosolapoff, "Organophosphorus Compounds", 1950, Wiley and Sons, pp. 180–199.

"Dictionary of Organophosphorus Compounds", edited by Edmundson, 1988, Chapman and Hall, pp. 144 and 149, entries C–00063 and C–00092.

Riesel et al., J. Z. Anorg. Allg. Chem., 603, 145 (1991).

Tullock et al., J. Org. Chem., 25, 2016 (1960).

White et al., J. Am. Chem. Soc., 92, 7125 (1970).

Meyer et al., Z. Naturforsch, Bi. Chem. Sci., 48, 659 (1993).

Dunlop, Jane E. et al., The Rhodium–Catalyzed Methanolysis of Aryl Acetates, Transition Met. Chem. 15 48–50, Dec. 1990.

*Primary Examiner*—Johann Richter
*Assistant Examiner*—Dominic Keating
*Attorney, Agent, or Firm*—Charles R. Martin; Harry J. Gwinnell

[57] ABSTRACT

Disclosed are catalyst systems comprising one or more transition metals selected from the Group VIII metals and rhenium and one or more fluorophosphite compounds having the general formula

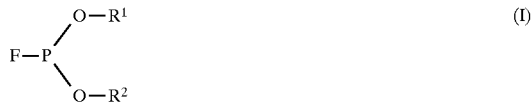

wherein $R^1$ and $R^2$ are hydrocarbyl radicals. Also disclosed are catalyst solutions comprising one or more the above fluorophosphite compounds, rhodium and a hydroformylation solvent, and hydroformylation processes wherein olefins are contacted with carbon monoxide, hydrogen and the catalyst solution to produce aldehydes.

21 Claims, No Drawings

HYDROFORMYLATION PROCESS USING NOVEL PHOSPHITE-METAL CATALYST SYSTEM

This invention pertains to certain novel catalyst systems comprising at least one fluorophosphite ligand compound in combination with a transition metal and the use of the catalyst system in the hydroformylation of various α-olefins to produce aldehydes.

The hydroformylation reaction, also known as the oxo reaction, is used extensively in commercial processes for the preparation of aldehydes by the reaction of one mole of an olefin with one mole each of hydrogen and carbon monoxide. The most extensive use of the reaction is in the preparation of normal- and iso-butyraldehyde from propylene. The ratio of the amount of the normal aldehyde product to the amount of the iso aldehyde product typically is referred to as the normal to iso (N:I) or the normal to branched (N:B) ratio. In the case of propylene, the normal- and iso-butyraldehydes obtained from propylene are in turn converted into many commercially-valuable chemical products such as, for example, n-butanol, 2-ethyl-hexanol, n-butyric acid, iso-butanol, neo-pentyl glycol, 2,2,4-trimethyl-1,3-pentanediol, the mono-isobutyrate and di-isobutyrate esters of 2,2,4-trimethyl-1,3-pentanediol. The hydroformylation of higher α-olefins such as 1-octene, 1-hexene and 1-decene yield aldehyde products which are useful feedstocks for the preparation of detergent alcohols and plasticizer alcohols. The hydroformylation of substituted olefins such as allyl alcohol is useful for the production of other commercially valuable products such as 1,4-butanediol.

U.S. Pat. No. 3,239,566, issued Mar. 8, 1966, to Slaugh and Mullineaux, discloses a low pressure hydro-formylation process using trialkylphosphines in combination with rhodium catalysts for the preparation of aldehydes. Trialkylphosphines have seen much use in industrial hydroformylation processes but they typically produce a limited range of products and, furthermore, frequently are very oxygen sensitive. U.S. Pat. No. 3,527,809, issued Sep. 8, 1970 to Pruett and Smith, discloses a low pressure hydroformylation process which utilizes triarylphosphine or triarylphosphite ligands in combination with rhodium catalysts. The ligands disclosed by Pruett and Smith, although used in many commercial applications, have limitations due to oxidative and hydrolytic stability problems. Since these early disclosures, numerous improvements have been made to increase the catalyst stability, catalyst activity and the product ratio with a heavy emphasis on yielding linear aldehyde product. A wide variety of monodentate phosphite and phosphine ligands, bidentate ligands such as bisphosphites and bisphosphines as well as tridentate and polydentate ligands have been prepared and disclosed in the literature. Notwithstanding the substantial progress which has been made in the area of hydroformylation catalyst systems and chemistry, there still exists a need to develop more stable, less expensive and more selective hydroformylation catalysts.

We have discovered that fluorophosphite diester compounds are useful as ligands in catalyst systems for the conversion of olefins to aldehydes. The fluorophosphite ligands of the present invention can be substituted for, or used in combination with, known phosphite and/or phosphine ligands in a wide variety of catalyst systems using a transition metal as the primary catalyst component. Thus, one embodiment of the present invention is a novel catalyst system comprising a combination of one or more transition metals selected from the Group VIII metals and rhenium and one or more fluorophosphite compounds having the general formula

wherein $R^1$ and $R^2$ are hydrocarbyl radicals which contain a total of up to about 40 carbon atoms and wherein the ratio of gram moles fluorophosphite ligand to gram atoms transition metal is at least 1:1. The novel catalyst systems may be used in a wide variety of transition metal-catalyzed processes such as, for example, hydro-formylation, hydrogenation, isomerization, hydrocyanation, hydrosilation, carbonylations, oxidations, acetoxylations, epoxidations, hydroamination, dihydroxylation, cyclopropanation, telomerizatons, carbon hydrogen bond activation, olefin metathesis, olefin dimerizations, oligomerizations, olefin polymerizations, olefin-carbon monoxide copolymerizations, butadiene dimerization and oligomerization, butadiene polymerization, and other carbon-carbon bond forming reactions such as the Heck reaction and arene coupling reactions. The catalyst systems comprising rhodium as the transition metal are especially useful for the hydroformylation of olefins to produce aldehydes and, therefore, are preferred.

A second embodiment of our invention concerns a novel catalyst solution comprising (1) one or more of the fluorophosphite ligands of formula (I), (2) rhodium and (3) a hydroformylation solvent. This embodiment comprises a solution of the active catalyst in which a carbonylation process such as the hydroformylation of an ethylenically-unsaturated compound may be carried out.

A third embodiment of the present invention pertains to a hydroformylation process utilizing the above-described catalyst systems and solutions. The process of the present invention therefore includes a process for preparing an aldehyde which comprises contacting an olefin, hydrogen and carbon monoxide with a solution of a catalyst system comprising rhodium and a fluorophosphite ligand of formula (I) wherein the mole ratio of phosphine ligand:rhodium is at least 1:1.

It is generally recognized in the art that the presence of halogens in hydroformylation catalysts normally reduces substantially the activity of the catalyst. The literature contains numerous references and citations where halogens are identified as poisons in the rhodium catalyzed hydroformylation process. For example, Falbe ("New Syntheses with Carbon Monoxide" edited by J. Falbe, 1980, Springer-Verlag) on page 73 lists halogens as poisons for hydroformylation catalysts. U.S. Pat. Nos. 5,059,710, 4,595,753, 4,605, 781 and 4,642,395 teach that halogen atoms generally are detrimental to the activity of hydroformylation catalyst systems. U.S. Pat. No. 4,871,878 discloses that halogens may be present in the organic structure of a ligand, but these halogen-containing substituents typically have the halogen located in a stable, non-hydrolyzable group, away from the phosphorus center and sufficiently far removed from the rhodium atom that no interactions can occur. For example, U.S. Pat. No. 4,871,878 teaches the use of halogen substituted tribenzylphosphine ligands except those cases where the chlorine, bromine or iodine are in the positions adjacent to the benzylic group.

Reactions of halophosphorus compounds with hydroxylic materials or water are well known in the chemical literature. Cotton and Wilkinson ("Advanced Inorganic Chemistry", 3rd Edition, 1972, Wiley and Sons, pages 374–375) describe the phosphorus halides as materials that are hydrolyzed, sometimes violently, in the presence of water. Kosolapoff reported many years ago ("Organophosphorus Compounds", 1950, Wiley and Sons, pages 180 to 199) that the halophosphites are unstable to heat, and react with water, alcohols, and phenols. Chlorophosphites have been characterized as "Rapidly hydrolyzed" and "Reacts violently with water" ("Dictionary Of Organophosphorus Compounds", edited by Edmundson, 1988, Chapman and Hall, pages 144 and 149, entries C-00063 and C-00092). The reactions with the hydroxylic materials generate phosphoric acid esters as the initial product and hydrogen halides. Hydrogen halides have been described as poisons to many transition metal-catalyzed processes such as the hydroformylation reaction. Therefore, the presence of any phosphorus halide species in a hydroformylation reaction usually is deemed undesirable.

Contrary to the teachings of the prior art, we have found that the fluorophosphite ester compounds having the formula

(I)

function as effective ligands when used in combination with transition metals to form catalyst systems for the processes described hereinabove. The hydrocarbyl groups represented by $R^1$ and $R^2$ may be the same or different, separate or combined, and are selected from unsubstituted and substituted alkyl, cycloalkyl and aryl groups containing a total of up to about 40 carbon atoms. The total carbon content of substituents $R^1$ and $R^2$ preferably is in the range of about 2 to 35 carbon atoms. Examples of the alkyl groups which $R^1$ and/or $R^2$ separately or individually can represent include ethyl, butyl, pentyl, hexyl, 2-ethylhexyl, octyl, decyl, dodecyl, octadecyl and various isomers thereof. The alkyl groups may be substituted, for example, with up to two substituents such as alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. Cyclopentyl, cyclohexyl and cycloheptyl are examples of the cycloalkyl groups $R^1$ and/or $R^2$ individually can represent. The cycloalkyl groups may be substituted with alkyl or any of the substituents described with respect to the possible substituted alkyl groups. The alkyl and cycloalkyl groups which $R^1$ and/or $R^2$ individually can represent preferably are alkyl of up to about 8 carbon atoms, benzyl, cyclopentyl, cyclohexyl or cycloheptyl.

Examples of the aryl groups which $R^1$ and/or $R^2$ individually can represent include carbocyclic aryl such as phenyl, naphthyl, anthracenyl and substituted derivatives thereof. Examples of the carbocyclic aryl groups which $R^1$ and/or $R^2$ individually can represent the radicals having the formulas

(II)

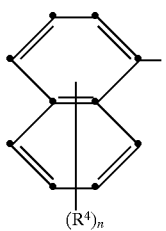
(III)

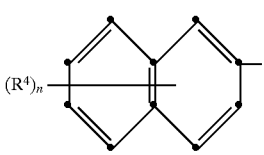
(IV)

wherein $R^3$ and $R^4$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts and the like. The alkyl moiety of the aforesaid alkyl, alkoxy, alkanoyl, alkoxycarbonyl and alkanoyloxy groups typically contains up to about 8 carbon atoms. Although it is possible for m to represent 0 to 5 and for n to represent 0 to 7, the value of each of m and n usually will not exceed 2. $R^3$ and $R^4$ preferably represent lower alkyl groups, i.e., straight-chain and branched-chain alkyl of up to about 4 carbon atoms, and m and n each represent 0, 1 or 2.

Alternatively, $R^1$ and $R^2$ in combination or collectively may represent a divalent hydrocarbylene group containing up to about 40 carbon atoms, preferably from about 12 to 36 carbon atoms. Examples of such divalent groups include alkylene of about 2 to 12 carbon atoms, cyclohexylene and arylene. Specific examples of the alkylene and cycloalkylene groups include ethylene, trimethylene, 1,3-butanediyl, 2,2-dimethyl-1,3-propanediyl, 1,1,2-triphenylethanediyl, 2,2,4-trimethyl-1,3-pentanediyl, 1,2-cyclohexylene, and the like. Examples of the arylene groups which $R^1$ and $R^2$ collectively may represent are given hereinbelow as formulas (V), (VI) and (VII).

The divalent groups that $R^1$ and $R^2$ collectively may represent include radicals having the formula

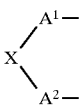

wherein
each of $A^1$ and $A^2$ is an arylene radical, e.g., a divalent, carbocyclic aromatic group containing 6 to 10 ring carbon atoms, wherein each ester oxygen atom of fluorophosphite (I) is bonded to a ring carbon atom of $A^1$ and $A^2$;
X is (i) a chemical bond directly between ring carbon atoms of $A^1$ and $A^2$; or (ii) an oxygen atom, a group having the formula —$(CH_2)_y$— wherein y is 2 to 4 or a group having the formula

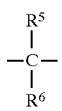

wherein $R^5$ is hydrogen, alkyl or aryl, e.g., the aryl groups illustrated by formulas (II), (III) and (IV), and R[6] is hydrogen or alkyl. The total carbon content of the group —C(R[5])(R[6])— normally will not exceed 20 and, preferably, is in the range of 1 to 8 carbon atoms. Normally, when R[1] and R[2] collectively represent a divalent hydrocarbylene group, the phosphite ester oxygen atoms, i.e. the oxygen atoms depicted in formula (I), are separated by a chain of atoms containing at least 3 carbon atoms.

Examples of the arylene groups represented by each of A[1] and A[2] include the divalent radicals having the formulas:

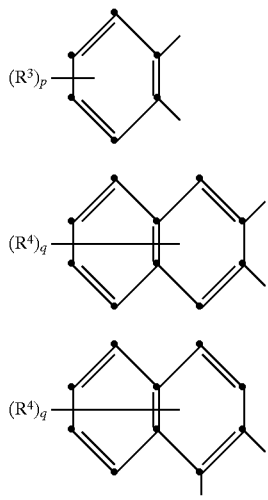

wherein R[3] and R[4] may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts and the like. The alkyl moiety of such alkyl, alkoxy, alkanoyl, alkoxycarbonyl and alkanoyloxy groups typically contains up to about 8 carbon atoms. Although it is possible for p to represent 0 to 4 and for q to represent 0 to 6, the value of each of p and q usually will not exceed 2. R[3] and R[4] preferably represent lower alkyl groups, i.e., straight-chain and branched-chain alkyl of up to about 4 carbon atoms, and p and q each represent 0, 1 or 2.

The fluorophosphite esters that are most preferred, e.g., those which exhibit the best stability, are those wherein the fluorophosphite ester oxygen atoms are bonded directly to a ring carbon atom of a carbocyclic, aromatic group, e.g., an aryl or arylene group represented by any of formulas (II) through (VII). When R[1] and R[2] individually each represents an aryl radical, e.g., a phenyl group, it is further preferred that 1 or both of the ring carbon atoms that are in a position ortho to the ring carbon atoms bonded to the fluorophosphite ester oxygen atom are substituted with an alkyl group, especially a branched chain alkyl group such as isopropyl, tert-butyl, tert-octyl and the like. Similarly, when R[1] and R[2] collectively represent a radical having the formula

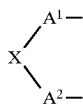

the ring carbon atoms of arylene radicals A[1] and A[2] that are in a position ortho to the ring carbon atoms bonded to the fluorophosphite ester oxygen atom are substituted with an alkyl group, preferably a branched chain alkyl group such as isopropyl, tert-butyl, tert-octyl and the like. The most preferred fluorophosphite esters have the general formula

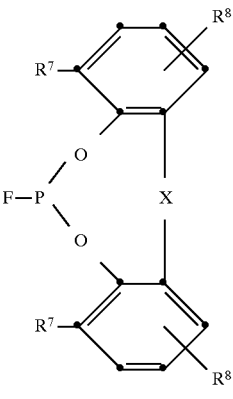

wherein each R[7] is alkyl of 3 to 8 carbon atoms; each R[8] is hydrogen, alkyl of 1 to 8 carbon atoms or alkoxy of 1 to 8 carbon atoms; and X is (i) a chemical bond directly between ring carbon atoms of each phenylene group to which X is bonded; or (ii) a group having the formula

wherein each of R[5] and R[6] is hydrogen or alkyl of 1 to 8 carbon atoms.

The fluorophosphite esters of formula (I) may be prepared by published procedures or by techniques analogous thereto. See, for example, the procedures described by Riesel et al., J. Z. Anorg. Allg. Chem., 603, 145 (1991), Tullock et al., J. Org. Chem., 25, 2016 (1960), White et al., J. Am. Chem. Soc., 92, 7125 (1970) and Meyer et al., Z. Naturforsch, Bi. Chem. Sci., 48, 659 (1993) and in U.S. Pat. No. 4,912,155. The organic moiety of the fluorophosphite compounds, i.e., the residue(s) represented by R[1] and R[2] can be derived from chiral or optically active compounds. Fluorophosphite ligands derived from chiral glycols or phenols will generate chiral ligands. Ligands consisting of the chiral fluorophosphites can be used in many transition metal catalyzed processes including, but not limited to, hydroformylation, hydrogenation, hydrocyanation, hydrosilation, carbonylations, oxidations, acetoxylations, epoxidations, hydroamination, dihydroxylation, cyclopropanation, carbon hydrogen bond activation, olefin metathesis, olefin dimerizations, olefin oligomerizations, olefin polymerizations, olefin-carbon monoxide copolymerizations, butadiene dimerization and oligomerization, butadiene polymerization, and other carbon-carbon bond forming reactions such as the Heck reaction to yield enantioselective product mixtures.

The novel catalyst systems provided by the present invention comprise a combination of one or more transition metals selected from the Group VIII metals and rhenium and one or more of the fluorophosphite compounds described in detail hereinabove. The transition metal may be provided in the form of various metal compounds such as carboxylate salts of the transition metal. Rhodium compounds that may be used as a source of rhodium for the active catalyst include rhodium II or rhodium III salts of carboxylic acids, examples of which include di-rhodium tetraacetate dihydrate, rhodium (II) acetate, rhodium(II) isobutyrate, rhodium(II) 2-ethylhexanoate, rhodium(II) benzoate and rhodium(II) octanoate. Also, rhodium carbonyl species such as $Rh_4(CO)$ $_{12}$, $Rh_6(CO)_{16}$ and rhodium(I) acetylacetonate dicarbonyl may be suitable rhodium feeds. Additionally, rhodium organophosphine complexes such as tris(triphenylphosphine) rhodium carbonyl hydride may be used when the phosphine moieties of the complex fed are easily displaced by the fluorophosphite ligands of the present invention. Less desirable rhodium sources are rhodium salts of strong mineral acids such as chlorides, bromides, nitrates, sulfates, phosphates and the like.

The ratio of gram moles fluorophosphite ligand to gram atoms transition metal can vary over a wide range, e.g., gram mole fluorophosphite:gram atom transition metal ratios of about 1:1 to 100:1. For the rhodium-containing catalyst systems the gram mole fluorophosphite:gram atom rhodium ratio preferably is in the range of about 1:1 up to 70:1 with ratios in the range of about 1:1 to 50:1 being particularly preferred.

A second embodiment of our invention concerns a novel catalyst solution comprising (1) one or more of the fluorophosphite ligands of formula (I), (2) rhodium and (3) a hydroformylation solvent. This embodiment comprises a solution of the active catalyst in which a carbonylation process such as the hydroformylation of an ethylenically-unsaturated compound may be carried out.

The hydroformylation reaction solvent may be selected from a wide variety of compounds, mixture of compounds, or materials that are liquid at the pressure at which the process is being operated. Such compounds and materials include various alkanes, cycloalkanes, alkenes, cycloalkenes, carbocyclic aromatic compounds, alcohols, esters, ketones, acetals, ethers and water. Specific examples of such solvents include alkane and cycloalkanes such as dodecane, decalin, octane, iso-octane mixtures, cyclohexane, cyclooctane, cyclododecane, methylcyclohexane; aromatic hydrocarbons such as benzene, toluene, xylene isomers, tetralin, cumene, alkyl-substituted aromatic compounds such as the isomers of diisopropylbenzene, triisopropylbenzene and tert-butylbenzene; alkenes and cycloalkenes such as 1,7-octadiene, dicyclopentadiene, 1,5-cyclooctadiene, octene-1, octene-2, 4-vinylcyclohexene, cyclohexene, 1,5,9-cyclododecatriene, 1-pentene; crude hydrocarbon mixtures such as naphtha, mineral oils and kerosene; high-boiling esters such as 2,2,4-trimethyl-1,3-pentanediol diisobutyrate. The aldehyde product of the hydroformylation process also may be used. In practice, the preferred solvent is the higher boiling by-products that are naturally formed during the process of the hydroformylation reaction and the subsequent steps, e.g., distillations, that are required for aldehyde product isolation. The main criteria for the solvent is that it dissolves the catalyst and olefin substrate and does not act as a poison to the catalyst. Preferred solvents for the production of volatile aldehydes, e.g., propionaldehyde and the butyraldehydes, are those that are sufficiently high boiling to remain, for the most part, in a gas sparged reactor. Solvents and solvent combinations that are preferred for use in the production of less volatile and non-volatile aldehyde products include 1-methyl-2-pyrrolidinone, dimethyl-formamide, perfluorinated solvents such as perfluoro-kerosene, sulfolane, water, and high boiling hydrocarbon liquids as well as combinations of these solvents. We have found that non-hydroxylic compounds, in general, and hydrocarbons, in particular, may be used advantageously as the hydroformylation solvent since their use can minimize decomposition of the fluorophosphite ester ligands.

The concentration of the rhodium and ligand in the hydroformylation solvent or reaction mixture is not critical for the successful operation of our invention. As mentioned hereinabove, a gram mole ligand:gram atom rhodium ratio of at least 1:1 normally is maintained in the reaction mixture. The absolute concentration of rhodium in the reaction mixture or solution may vary from 1 mg/liter up to 5000 mg/liter or more. When the process is operated within the practical conditions of this invention, the concentration of rhodium in the reaction solution normally is in the range of about 20 to 300 mg/liter. Concentrations of rhodium lower than this range generally do not yield acceptable reaction rates with most olefin reactants and/or require reactor operating temperatures that are so high as to be detrimental to catalyst stability. Higher rhodium concentrations are not preferred because of the high cost of rhodium.

No special or unusual techniques are required for preparing the catalyst systems and solutions of the present invention, although it is preferred, to obtain a catalyst of high activity, that all manipulations of the rhodium and fluorophosphite ligand components be carried out under an inert atmosphere, e.g., nitrogen, argon and the like. The desired quantities of a suitable rhodium compound and ligand are charged to the reactor in a suitable solvent. The sequence in which the various catalyst components or reactants are charged to the reactor is not critical.

The third embodiment of the present invention pertains to a hydroformylation process utilizing the above-described catalyst systems and solutions. The process of the present invention therefore is a process for preparing an aldehyde which comprises contacting an olefin, hydrogen and carbon monoxide with a solution of a catalyst system comprising rhodium and a fluorophosphite ligand of formula (I) wherein the ratio of gram moles ligand:gram atom rhodium is at least 1:1. The olefins that may be hydroformylated by means of our novel process comprise aliphatic, including ethylenically-unsaturated, low molecular weight polymers, alicyclic, aromatic and heterocyclic mono-, di- and tri-olefins containing up to about 40 carbon atoms. Examples of the aliphatic olefins that may be utilized in the process include straight- and branched-chain, unsubstituted and substituted, aliphatic mono-α-olefins containing up to about 20 carbon atoms. Examples of the groups that may be present on the substituted mono-α-olefins include hydroxy; alkoxy including ethers and acetals; alkanoyloxy such as acetoxy; amino including substituted amino; carboxy; alkoxycarbonyl; carboxamido; keto; cyano; and the like. Preferred aliphatic mono-α-olefins have the general formulas:

$$H_2C=CH-R^7 \text{ and } H_2C=CH-R^8-R^9$$

wherein
$R^7$ is hydrogen or straight- or branched-chain alkyl of up to about 8 carbon atoms;
$R^8$ is straight- or branched-chain alkylene of up to about 18 carbon atoms; and
$R^9$ is hydroxy, alkoxy of up to about 4 carbon atoms, alkanoyloxy of up to about 4 carbon atoms, carboxyl or alkoxycarbonyl of 2 to about 10 carbon atoms.

Specific examples of the aliphatic mono-α-olefins include ethylene, propylene, 1-butene, 1-octene, allyl alcohol and 3-acetoxy-1-propene.

The aliphatic, di-olefins may contain up to about 40 carbon atoms. Preferred aliphatic, di-olefins have the general formula:

$$H_2C=CH-R^{10}-CH=CH_2$$

wherein $R^{10}$ is straight- or branched-chain alkylene having 1 to about 18 carbon atoms.

The cyclic olefins which may be used in the hydroformylation process of the present invention may be cycloalkenes, e.g., cyclohexene, 1,5-cyclooctadiene, and cyclodecatriene, and from various vinyl-substituted cycloalkanes, cycloalkenes, heterocyclic and aromatic compounds. Examples of such cyclic olefins include 4-vinylcyclohexene, 1,3-cyclohexadiene, 4-cyclohexene-carboxylic acid, methyl 4-cyclohexene-carboxylic acid, 1,4-cyclooctadiene and 1,5,9-cyclododecatriene. The olefin reactants which are particularly preferred comprise mono-α-olefins of 2 to 10 carbon atoms, especially propylene.

Mixtures of olefins can also be used in the practice of this invention. The mixtures may be of the same carbon number such as mixtures of n-octenes or it may represent refinery distillation cuts which will contain a mixture of olefins over a range of several carbon numbers.

The reaction conditions used are not critical for the operation of the process and conventional hydroformylation conditions normally are used. The process requires that an olefin is contacted with hydrogen and carbon monoxide in the presence of the novel catalyst system described hereinabove. While the process may be carried out at temperatures in the range of about 20° to 200° C., the preferred hydroformylation reaction temperatures are from 50° to 135° C. with the most favored reaction temperatures ranging from 75° to 125° C. Higher reactor temperatures are not favored because of increased rates of catalyst decomposition while lower reactor temperatures result in relatively slow reaction rates. The total reaction pressure may range from about ambient or atmospheric up to 70 bars absolute (about 1000 psig), preferably from about 8 to 28 bars absolute (about 100 to 400 psig).

The hydrogen:carbon monoxide mole ratio in the reactor likewise may vary considerably ranging from 10:1 to 1:10 and the sum of the absolute partial pressures of hydrogen and carbon monoxide may range from 0.3 to 36 bars absolute. The partial pressures of the ratio of the hydrogen to carbon monoxide in the feed is selected according to the linear:branched isomer ratio desired. Generally, the partial pressure of hydrogen and carbon monoxide in the reactor is maintained within the range of about 1.4 to 13.8 bars absolute (about 20 to 200 psia) for each gas. The partial pressure of carbon monoxide in the reactor is maintained within the range of about 1.4 to 13.8 bars absolute (about 20 to 200 psia) and is varied independently of the hydrogen partial pressure. The molar ratio of hydrogen to carbon monoxide can be varied widely within these partial pressure ranges for the hydrogen and carbon monoxide. The ratios of the hydrogen to carbon monoxide and the partial pressure of each in the synthesis gas (syngas—carbon monoxide and hydrogen) can be readily changed by the addition of either hydrogen or carbon monoxide to the syngas stream. We have found that with the fluorophosphite ligands described herein, the ratio of linear to branched products can be varied widely by changing the partial pressures of the carbon monoxide in the reactor.

The amount of olefin present in the reaction mixture also is not critical. For example, relatively high-boiling olefins such as 1-octene may function both as the olefin reactant and the process solvent. In the hydroformylation of a gaseous olefin feedstock such as propylene, the partial pressures in the vapor space in the reactor typically are in the range of about 0.07 to 35 bars absolute. In practice the rate of reaction is favored by high concentrations of olefin in the reactor. In the hydroformylation of propylene, the partial pressure of propylene preferably is greater than 1.4 bars, e.g., from about 1.4 to 10 bars absolute. In the case of ethylene hydroformylation, the preferred partial pressure of ethylene in the reactor is greater than 0.14 bars absolute.

Any of the known hydroformylation reactor designs or configurations may be used in carrying out the process provided by the present invention. Thus, a gas-sparged, vapor take-off reactor design as disclosed in the examples set forth herein may be used. In this mode of operation, the catalyst which is dissolved in a high boiling organic solvent under pressure does not leave the reaction zone with the aldehyde product taken overhead by the unreacted gases. The overhead gases then are chilled in a vapor/liquid separator to liquify the aldehyde product and the gases can be recycled to the reactor. The liquid product is let down to atmospheric pressure for separation and purification by conventional technique. The process also may be practiced in a batchwise manner by contacting the olefin, hydrogen and carbon monoxide with the present catalyst in an autoclave.

A reactor design where catalyst and feedstock are pumped into a reactor and allowed to overflow with product aldehyde, i.e. liquid overflow reactor design, is also suitable. For example, high boiling aldehyde products such a nonyl aldehydes may be prepared in a continuous manner with the aldehyde product being removed from the reactor zone as a liquid in combination with the catalyst. The aldehyde product may be separated from the catalyst by conventional means such as by distillation or extraction and the catalyst then recycled back to the reactor. Water soluble aldehyde products, such as hydroxy butyraldehyde products obtained by the hydroformylation of allyl alcohol, can be separated from the catalyst by extraction techniques. A trickle-bed reactor design also is suitable for this process. It will be apparent to those skilled in the art that other reactor schemes may be used with this invention.

The various embodiments of the present invention are further illustrated by the following examples. The hydroformylation process in which propylene is hydroformylated to produce butyraldehydes is carried out in a vapor take-off reactor consisting of a vertically arranged stainless steel pipe having a 2.5 cm inside diameter and a length of 1.2 meters. The reactor has a filter element welded into the side down near the bottom of the reactor for the inlet of gaseous reactants. The reactor contains a thermowell which is arranged axially with the reactor in its center for accurate measurement of the temperature of the hydroformylation reaction mixture. The bottom of the reactor has a high pressure tubing connection that is connected to a cross. One of the connections to the cross permits the addition of non-gaseous reactants such as octene-1 or make-up solvent, another leads to the high-pressure connection of a differential pressure (D/P) cell that is used to measure catalyst level in the reactor and the bottom connection is used for draining the catalyst solution at the end of the run.

In the hydroformylation of propylene in a vapor take-off mode of operation, the hydroformylation reaction mixture or solution containing the catalyst is sparged under pressure with the incoming reactants of propylene, hydrogen and carbon monoxide as well as any inert feed such as nitrogen. As butyraldehyde is formed in the catalyst solution, it and unreacted reactant gases are removed as a vapor from the top of the reactor by a side-port. The vapor removed is chilled in a high pressure separator where the butyraldehyde product is condensed along with some of the unreacted propylene. The uncondensed gases are let down to atmospheric pressure via the pressure control valve. These gases pass through a series of dry-ice traps where any other aldehyde product is collected. The product from the high pressure separator is combined with that of the traps, and is subsequently weighed and analyzed by standard gas/liquid phase chromatography (GLC) techniques for the net weight and normal/iso ratio of the butyraldehyde product.

The gaseous feeds to the reactor are fed to the reactor via twin cylinder manifolds and high pressure regulators. The hydrogen passes through a commercially available Deoxo® (registered trademark of Engelhard Inc.) catalyst bed to remove any oxygen contamination and through a flow controller D/P cell and control valve. The carbon monoxide passes through a similar Deoxo® bed heated to 125° C., an iron carbonyl removal bed (as disclosed in U.S. Pat. No. 4,608,239). Nitrogen can be added to the feed mixture as an inert gas. Nitrogen, when added, is metered and then mixed with the hydrogen feed prior to the hydrogen Deoxo® bed. Propylene is fed to the reactor from feed tanks that are pressurized with hydrogen and is controlled using an armored rotameter in combination with a needle control valve. Propylene feed rate is measured by the rate of level drop in the tank in conjunction with the rotameter control point. All gases and propylene are passed through a preheater to insure vaporization of the liquid propylene leaving the armored rotameter.

The hydroformylation of a higher-boiling, liquid olefin, 1-octene, is carried out in a high pressure autoclave. The olefin, catalyst, and solvent are sealed in the autoclave under nitrogen. The reaction mixture then is pressurized with hydrogen and carbon monoxide and heated to the desired reaction temperature. The autoclave is maintained at reaction temperature and pressure selected for a predetermined amount of time or until gas uptake ceases. The autoclave then is cooled to ambient temperature and vented. The contents of the autoclave are recovered and analyzed for olefin and aldehyde content by conventional gas chromatography.

EXAMPLE 1

A catalyst solution was prepared under nitrogen using a charge of 15 mg of rhodium charged as a rhodium (II) dicarbonylacetonyl acetate (0.145 mmole, 0.0375 g), 2,2'-ethylidene bis(4,6-di-tert-butylphenyl) fluoro-phosphite (4.35 mmole, 2.11 grams) having the structure

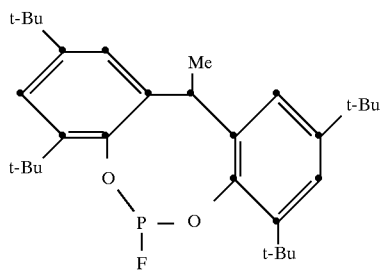

(t-Bu=tertiary butyl; Me=methyl) and 190 mL of 2,2,4-trimethyl-1,3- pentanediol monoisobutyrate solvent. This catalyst solution was charged to the reactor under an argon blanket and the reactor sealed. The reactor was pressured to 18.9 bars absolute (260 psig) with hydrogen, carbon monoxide and nitrogen and heated to 115° C. Propylene feed then was started and the flows were adjusted to the following reported as liters/minute at standard temperature and pressure (STP): hydrogen=3.70; carbon monoxide=3.70; nitrogen=1.12 and propylene=2.08. This is equivalent to having the following partial pressures in the feed to the reactor reported as bars absolute (psia): hydrogen=6.6 (96); carbon monoxide=6.6 (96); nitrogen=2 (29); and propylene=3.7 (54).

The reaction was carried out under the above flows for 5 hours. The butyraldehyde production rate for the last 3 hours of operation averaged 92.5 g/hour for a catalyst activity of 5.86 kilograms butyraldehyde/gram of rhodium-hour. The product N:Iso ratio was 3.3:1.

EXAMPLE 2

This example illustrates the effect of using a lower carbon monoxide partial pressure in the hydroformylation of propylene. A catalyst solution was prepared under nitrogen using a charge of 15 mg of rhodium charged as a rhodium (II) dicarbonylacetonyl acetate (0.145 mmole, 0.0375 g), 2,2'-ethylidene bis(4,6-di-tert-butylphenyl) fluorophosphite (4.35 mmole, 2.11 g) and 190 mL of 2,2,4-trimethyl-1,3-pentanediol monoisobutyrate solvent. The mixture was charged to the reactor under an argon blanket and the reactor sealed. The reactor was pressured to 18.9 bars absolute (260 psig) with hydrogen, carbon monoxide and nitrogen and heated to 115° C. Propylene feed then was started and the flows were adjusted to the following values reported as liters/minute at standard temperature and pressure (STP): hydrogen=3.80; carbon monoxide=1.90; nitrogen=1.93 and propylene=1.87. This is equivalent to having the following partial pressures in the feed to the reactor reported as bars absolute (psia): hydrogen=7.6 (110); carbon monoxide=3.8 (55); nitrogen=3.9 (56); and propylene=3.7 (54).

The process was operated for 5 hours using the above flows. The butyraldehyde production rate for the last 3 hours of operation averaged 60.6 g/hour for a catalyst activity of 3.86 kilograms butyraldehyde/gram of rhodium-hour. The product N:Iso ratio was 4.0:1.

EXAMPLE 3

A catalyst solution was prepared under nitrogen using a charge of 15 mg of rhodium charged as a rhodium (II) dicarbonylacetonyl acetate (0.145 mmole, 0.0375 g), 2,2'-ethylidene bis(4,6-di-tert-butylphenyl) fluoro-phosphite (4.35 mmole, 2.11 g) and 90 mL of 2,2,4-trimethyl-1,3-pentanediol monoisobutyrate solvent. The catalyst solution and 10 mL of purified 1-octene were charged to a 300 mL, high pressure autoclave under a nitrogen blanket. The reactor was sealed and then pressurized to 28.6 bars absolute (400 psig) with a 1:1 mixture of hydrogen and carbon monoxide. The reactor was heated to 110° C. and maintained between 21.7 to 28.6 bars absolute (300–400 psig) by the addition of a 1:1 mixture of hydrogen and carbon monoxide. When the uptake of gas ceased, the reactor was cooled, vented, and the contents analyzed. Gas chromatography of the recovered liquid revealed that 92 mole percent of the 1-octene reactant had been converted to a mixture of nonyl aldehydes. The nonyl aldehyde fraction had a normal to branched isomer ratio of 4.21:1.

EXAMPLE 4

This example illustrates the hydroformylation of the substituted olefin, methyl methacrylate. A catalyst solution was prepared under nitrogen using 15 mg of rhodium charged as a rhodium (II) dicarbonylacetonyl acetate (0.145 mmole, 0.0375 g), 2,2'-ethylidene bis(4,6-di-tert-butylphenyl) fluorophosphite (4.35 mmole, 2.11 g) and 100 mL of toluene as solvent. This solution was charged to a 300 mL, high pressure auto-clave under an nitrogen blanket along with 10 mL of methyl methacrylate. The reactor was sealed and then pressurized to 28.6 bars absolute (400 psig) with a 1:1 mixture of hydrogen and carbon monoxide. The reactor was heated to 110° C. and maintained between 21.7 to 28.6 bars absolute (300–400 psig) by the addition of a 1:1 mixture of hydrogen and carbon monoxide. When the uptake of gas ceased, the reactor was cooled, vented, and the contents analyzed. Gas chromatography of the recovered liquid revealed that 43 mole percent of the methyl methacrylate had been converted to a mixture of methyl isobutyrate, methyl (2-methyl-3-formyl)propionate and methyl (2-methyl-2-formyl)propionate. The hydrogenation product, methyl isobutyrate, was 3% of the product. The aldehyde fraction was 97% of the products formed and had a predominance of the more linear isomer, methyl (2-methyl-3-formyl)-propionate, with the ratio to the less linear isomer being 2.63:1.

EXAMPLE 5

This example illustrates the hydroformylation of a mixture of cis and trans 2-octene. A catalyst solution was prepared under nitrogen using 15 mg of rhodium charged as a rhodium (II) dicarbonylacetonyl acetate (0.145 mmole, 0.0375 g), 2,2'-ethylidene bis(4,6-di-tert-butylphenyl) fluorophosphite (4.35 mmole, 2.11 g) and 90 mL of 2,2,4-trimethyl-1,3-pentanediol monoisobutyrate solvent. The catalyst solution thus prepared was charged to a 300 mL, high pressure autoclave under a nitrogen blanket along with 4.5 g of a mixture of cis- and trans-2-octene. The reactor was sealed and pressurized to 28.6 bars absolute (400 psig) with a 1:1 mixture of hydrogen and carbon monoxide. The reactor was heated to 110° C. and maintained between 21.7 to 28.6 bars absolute (300–400 psig) by the addition of a 1:1 mixture of hydrogen and carbon monoxide. When the uptake of gas ceased, the reactor was cooled, vented, and the contents analyzed. Gas chromatography of the recovered liquid revealed that 71 mole percent of the octene had been converted to a mixture of nonyl aldehydes. The nonyl aldehyde product had a normal to branched isomer ratio of 0.63:1.

EXAMPLE 6

This example illustrates the hydroformylation of propylene at higher carbon monoxide partial pressures and demonstrates catalyst stability. A catalyst solution was prepared under nitrogen using 15 mg of rhodium charged as a rhodium (II) dicarbonylacetonyl acetate (0.145 mmole, 0.0375 g), 2,2'-ethylidene bis(4,6-di-tert-butylphenyl) fluorophosphite (4.35 mmole, 2.11 g) and 190 mL of 2,2,4-trimethyl-1,3-pentanediol monoisobdtyrate solvent. The catalyst solution was charged to the reactor under an argon blanket and the reactor sealed. The reactor was pressured to 18.9 bars absolute (260 psig) with hydrogen, carbon monoxide and nitrogen and heated to 115° C. Propylene feed was then started and the flows were adjusted to the following values reported as liters/minute at standard temperature and pressure (STP): hydrogen=3.70; carbon monoxide=3.70; nitrogen=1.12 and propylene=2.08. This is equivalent to having the following partial pressures in the feed to the reactor reported as bars absolute (psia): hydrogen=6.6 (96); carbon monoxide=6.6 (96); nitrogen=2 (29); and propylene= 3.7 (54).

The process was operated at these conditions for a period of 48 hours and then the feed gas composition was changed to the following partial pressures, reported as bars absolute (psia): hydrogen=3.8 (55); carbon monoxide=7.6 (110); nitrogen=3.9 (56); and propylene=3.7 (54). The total gas flow to the reactor was 9.6 liters per minute. The reactor was operated until steady operations were achieved. The butyraldehyde production rate for the last 3 hours of operation averaged 59.2 g/hour for a catalyst activity of 3.8 kilograms butyraldehyde/gram of rhodium-hour. The N:Iso ratio of the product was 2.46:1.

EXAMPLE 7

A catalyst solution was prepared under nitrogen using a charge of 15 mg of rhodium charged as a rhodium (II) dicarbonylacetonyl acetate (0.145 mmole, 0.0375 g), 2,2'-methylene bis(4-methyl-6-tert-butylphenyl) fluorophosphite (1.94 mmole, 0.75 grams) having the structure

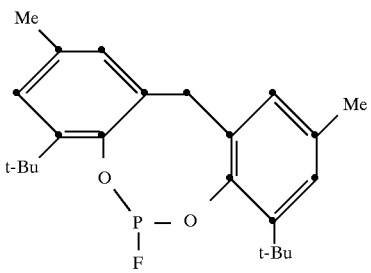

(Me=methyl) and 190 mL of 2,2,4-trimethyl-1,3-pentanediol monoisobutyrate solvent. This catalyst solution was charged to the reactor under an argon blanket and the reactor sealed. The reactor was pressured to 18.9 bars absolute (260 psig) with hydrogen, carbon monoxide and nitrogen and heated to 115° C. Propylene feed then was started and the flows were adjusted to the following reported as liters/minute at standard temperature and pressure (STP): hydrogen=3.70; carbon monoxide=3.70; nitrogen=1.12 and propylene=2.08. This is equivalent to having the following partial pressures in the feed to the reactor reported as bars absolute (psia): hydrogen=6.6 (96); carbon monoxide=6.6 (96); nitrogen=2 (29); and propylene=3.7 (54).

The reaction was carried out under the above flows for 5 hours. The butyraldehyde production rate for the last 3 hours of operation averaged 264 g/hour for a catalyst activity of 25.1 kilograms butyraldehyde/gram of rhodium-hour. The product N:Iso ratio was 1.44:1.

EXAMPLE 8

A catalyst solution was prepared under nitrogen using a charge of 15 mg of rhodium charged as a rhodium (II) dicarbonylacetonyl acetate (0.145 mmole, 0.0375 g), the fluorophosphite (2.91 mmole, 1.18 grams) having the structure

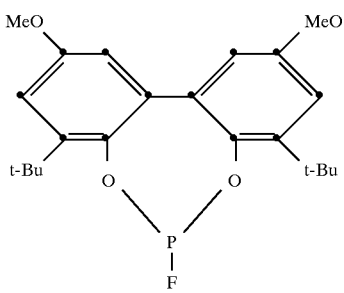

(Me=methyl) and 190 mL of 2,2,4-trimethyl-1,3-pentanediol monoisobutyrate solvent. This catalyst solution was charged to the reactor under an argon blanket and the reactor sealed. The reactor was pressured to 18.9 bars absolute (260 psig) with hydrogen, carbon monoxide and nitrogen and heated to 115° C. Propylene feed then was started and the flows were adjusted to the following reported as liters/ minute at standard temperature and pressure (STP): hydrogen=3.70; carbon monoxide=3.70; nitrogen=1.12 and propylene=2.08. This is equivalent to having the following partial pressures in the feed to the reactor reported as bars absolute (psia): hydrogen=6.6 (96); carbon monoxide=6.6 (96); nitrogen=2 (29); and propylene=3.7 (54).

The reaction was carried out under the above flows for 5 hours. The butyraldehyde production rate for the last 3 hours of operation averaged 99.5 g/hour for a catalyst activity of 9.6 kilograms butyraldehyde/gram of rhodium-hour. The product N:Iso ratio was 1.59:1.

EXAMPLE 9

A catalyst solution was prepared under nitrogen using a charge of 15 mg of rhodium charged as a rhodium (II) dicarbonylacetonyl acetate (0.145 mmole, 0.0375 g), bis(2, 4-di-tert-butylphenyl) fluorophosphite (4.37 mmole, 2.01 grams) and 190 mL of a NORPAR 13 paraffin solvent. NORPAR 13 is a paraffinic hydrocarbon solvent marketed by Exxon Chemical with a boiling point range of approximately 221° to 232° C. This catalyst solution was charged to the reactor under an argon blanket and the reactor sealed. The reactor was pressured to 18.9 bars absolute (260 psig) with hydrogen, carbon monoxide and nitrogen and heated to 115° C. Propylene feed then was started and the flows were adjusted to the following reported as liters/minute at standard temperature and pressure (STP): hydrogen=3.70; carbon monoxide=3.70; nitrogen=1.12 and propylene=2.08. This is equivalent to having the following partial pressures in the feed to the reactor reported as bars absolute (psia): hydrogen=6.6 (96); carbon monoxide=6.6 (96); nitrogen=2 (29); and propylene=3.7 (54).

The reaction was carried out under the above flows for 5 hours. The butyraldehyde production rate for the last 3 hours of operation averaged 121.9 g/hour for a catalyst activity of 7.41 kilograms butyraldehyde/gram of rhodium-hour. The product N:Iso ratio was 2.30:1.

EXAMPLE 10

A catalyst solution was prepared under nitrogen using a charge of 15 mg of rhodium charged as a rhodium (II) dicarbonylacetonyl acetate (0.145 mmole, 0.0375 g), the fluorophosphite (4.37 mmole, 2.00 grams) having the formula

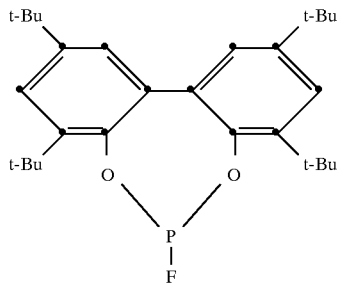

and 190 mL of a paraffin solvent (Norpar 13, Exxon Chemical Company). This catalyst solution was charged to the reactor under an argon blanket and the reactor sealed. The reactor was pressured to 18.9 bars absolute (260 psig) with hydrogen, carbon monoxide and nitrogen and heated to 115° C. Propylene feed then was started and the flows were adjusted to the following reported as liters/minute at standard temperature and pressure (STP): hydrogen=3.70; carbon monoxide=3.70; nitrogen=1.12 and propylene=2.08. This is equivalent to having the following partial pressures in the feed to the reactor reported as bars absolute (psia): hydrogen=6.6 (96); carbon monoxide=6.6 (96); nitrogen=2 (29); and propylene=3.7 (54).

The reaction was carried out under the above flows for 5 hours. The butyraldehyde production rate for the last 3 hours of operation averaged 51.9 g/hour for a catalyst activity of 2.82 kilograms butyraldehyde/gram of rhodium-hour. The product N:Iso ratio was 1.38:1.

EXAMPLE 11

A catalyst solution was prepared under nitrogen using a charge of 15 mg of rhodium charged as a rhodium (II) dicarbonylacetonyl acetate (0.145 mmole, 0.0375 g), bis(2, 4-di-tert-butylphenyl) fluorophosphite (4.37 mmole, 2.01 grams) and 190 mL of a mixed solvent composed of diphenyl ether and ISOPAR M in a 1.6 to 1 (volume:volume) ratio. ISOPAR M is a isoparaffin solvent marketed by Exxon Chemical with a boiling point range of 206° to 253° C. This catalyst solution was charged to the reactor under an argon blanket and the reactor sealed. The reactor was pressured to 18.9 bars absolute (260 psig) with hydrogen, carbon monoxide and nitrogen and heated to 115° C. Propylene feed then was started and the flows were adjusted to the following reported as liters/minute at standard temperature and pressure (STP): hydrogen=3.70; carbon monoxide=3.70; nitrogen=1.12 and propylene=2.08. This is equivalent to having the following partial pressures in the feed to the reactor reported as bars absolute (psia): hydrogen=6.6 (96); carbon monoxide=6.6 (96); nitrogen=2 (29); and propylene= 3.7 (54).

The reaction was carried out under the above flows for 4 hours. The butyraldehyde production rate for the last 3 hours of operation averaged 147.6 g/hour for a catalyst activity of 9.05 kilograms butyraldehyde/gram of rhodium-hour. The product N:Iso ratio was 2.21:1.

COMPARATIVE EXAMPLE 1

This example illustrates an attempt to hydroformylate 1-octene using an analogous chlorophosphite ligand. A catalyst solution was prepared under nitrogen using 15 mg of rhodium charged as a rhodium (II) dicarbonylacetonyl acetate (0.145 mmole, 0.0375 g), 1,1'-biphenol-2,2'-diylphosphachloridite (4.35 mmole, 1.09 g) having the structure

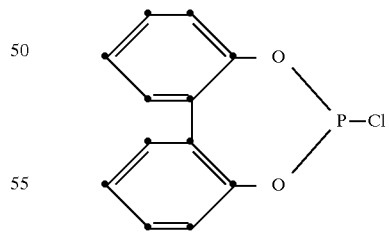

and 90 mL of 2,2,4-trimethyl-1,3-pentanediol monoisobutyrate solvent. This was charged to a 300 ml, high pressure autoclave under a nitrogen blanket along with 10 mL of purified 1-octene. The reactor was sealed and then pressurized to 28.6 bars absolute (400 psig) with a 1:1 mixture of hydrogen and carbon monoxide. The reactor was heated to and maintained at 110° C. These conditions were maintained for 2 hours without the uptake of any gas. The reactor was cooled, vented, and the contents analyzed. Gas chromatography of the recovered liquid revealed that no aldehyde products had been formed.

The invention has been described in detail with particular reference to preferred embodiments thereof, but it will be understood that variations and modifications will be effected within the spirit and scope of the invention.

We claim:

1. A catalyst composition comprising one or more transition metals selected from the Group VIII metals and rhenium and one or more fluorophosphite compounds having the general formula

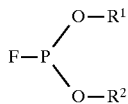

(I)

wherein $R^1$ and $R^2$ are hydrocarbyl radicals which contain a total of up to about 40 carbon atoms and wherein the ratio of gram moles fluorophosphite ligand to gram atoms transition metal is at least 1:1.

2. A catalyst composition according to claim 1 wherein the transition metal is rhodium and the total carbon atom content of the hydrocarbyl radicals represented by $R^1$ and $R^2$ is about 2 to 35.

3. A catalyst composition comprising rhodium and one or more fluorophosphite compounds having the general formula

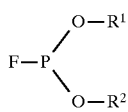

(I)

wherein $R^1$ and $R^2$ individually are independently selected from alkyl of up to about 8 carbon atoms, benzyl, cyclopentyl, cyclohexyl, cycloheptyl or an aryl group having the formula:

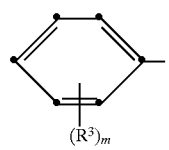

(II)

(III)

(IV)

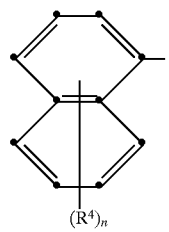

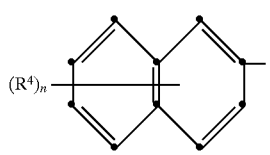

wherein $R^3$ and $R^4$ are independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of such alkyl, alkoxy, alkanoyl, alkoxycarbonyl and alkanoyloxy groups contains up to about 8 carbon atoms; m and n each is 0, 1 or 2; and the total carbon atom content of the hydrocarbyl radicals represented by $R^1$ and $R^2$ is about 2 to 35 and wherein the ratio of gram moles fluorophosphite ligand to gram atoms rhodium is about 1:1 to 70:1.

4. A catalyst composition comprising rhodium and one or more fluorophosphite compounds having the general formula

(I)

wherein $R^1$ and $R^2$ collectively represent a divalent hydrocarbylene group containing about 2 to 35 carbon atoms and wherein the ratio of gram moles fluorophosphite ligand to gram atoms transition metal is at least 1:1.

5. The catalyst composition according to claim 4 wherein the ratio of gram moles fluorophosphite ligand to gram atoms rhodium is about 1:1 to 70:1 and $R^1$ and $R^2$ collectively represent alkylene of about 2 to 12 carbon atoms, cyclohexylene, an arylene group having the formula

(V)

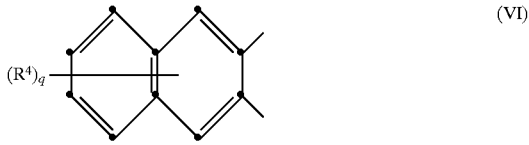

(VI)

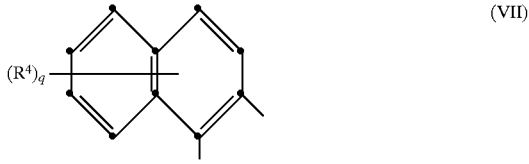

(VII)

or a radical having the formula

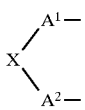

wherein
each of $A^1$ and $A^2$ is an arylene radical having formula (V), (VI) or (VII) above wherein each ester oxygen atom of fluorophosphite (I) is bonded to a ring carbon atom of $A^1$ and $A^2$;

X is (i) a chemical bond directly between ring carbon atoms of $A^1$ and $A^2$; or (ii) an oxygen atom, a group having the formula $-(CH_2)_y-$ wherein y is 2 to 4 or a group having the formula

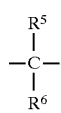

wherein $R^5$ is hydrogen, alkyl or aryl; $R^6$ is hydrogen or alkyl; and the group $-C(R^5)(R^6)-$ contains up to about 8 carbon atoms; and wherein $R^3$ and $R^4$ are independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of such alkyl, alkoxy, alkanoyl, alkoxycarbonyl and alkanoyloxy groups contains up to about 8 carbon atoms; p and q each is 0, 1 or 2.

6. The catalyst composition according to claim 5 wherein the fluorophosphite ligand has the formula

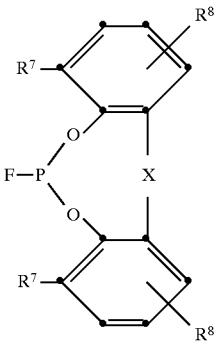

wherein each $R^7$ is alkyl of 3 to 8 carbon atoms; each $R^8$ is hydrogen, alkyl of 1 to 8 carbon atoms or alkoxy of 1 to 8 carbon atoms; and X is (i) a chemical bond directly between ring carbon atoms of each phenylene group to which X is bonded; or (ii) a group having the formula

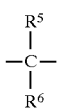

wherein each of $R^5$ and $R^6$ is hydrogen or alkyl of 1 to 8 carbon atoms and the ratio of gram moles fluorophosphite ligand to gram atoms rhodium is about 1:1 to 50:1.

7. The catalyst composition according to claim 6 wherein the fluorophosphite ligand has the formula

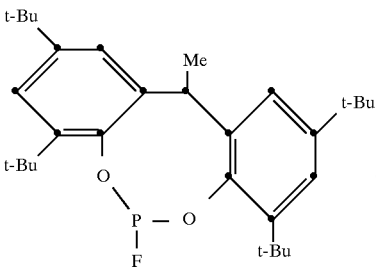

8. A catalyst solution comprising
(1) one or more fluorophosphite compounds having the general formula

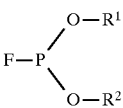  (I)

wherein $R^1$ and $R^2$ are hydrocarbyl radicals which contain a total of up to about 40 carbon atoms;
(2) rhodium; and
(3) a hydroformylation solvent;

wherein the ratio of gram moles fluorophosphite ligand to gram atoms rhodium is at least 1:1.

9. The catalyst solution according to claim 8 wherein the fluorophosphite compounds have the general formula

  (I)

wherein $R^1$ and $R^2$ individually are independently selected from alkyl of up to about 8 carbon atoms, benzyl, cyclopentyl, cyclohexyl, cycloheptyl or an aryl group having the formula:

  (II)

  (III)

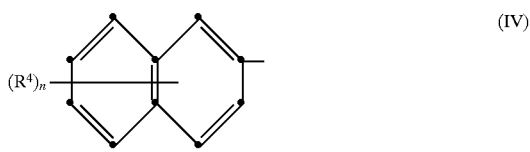  (IV)

wherein $R^3$ and $R^4$ are independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of such alkyl, alkoxy, alkanoyl, alkoxycarbonyl and alkanoyloxy groups contains up to about 8 carbon atoms; m and n each is 0, 1 or 2; and the total carbon atom content of the hydrocarbyl radicals represented by $R^1$ and $R^2$ is about 2 to 35 and wherein the ratio of gram moles fluorophosphite ligand to gram atoms rhodium is about 1:1 to 70:1.

10. The catalyst solution according to claim 9 wherein the ratio of gram moles fluorophosphite ligand to gram atoms rhodium is about 1:1 to 50:1 and the hydroformylation solvent is selected from alkanes, cycloalkanes, alkenes, cycloalkenes, carbocyclic aromatic compounds, esters, ketones, acetals and ethers and water which are liquid at the pressure at which the process is being operated.

11. The catalyst solution according to claim 8 wherein the fluorophosphite compounds have the general formula

  (I)

wherein $R^1$ and $R^2$ collectively represent alkylene of about 2 to 12 carbon atoms, cyclohexylene, an arylene group having the formula

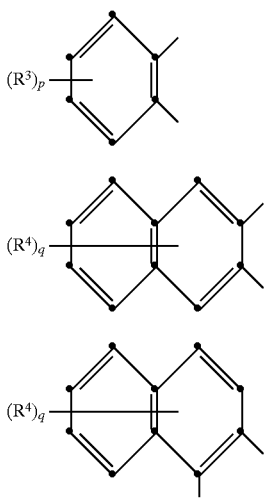

or a radical having the formula

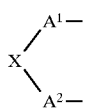

wherein
each of $A^1$ and $A^2$ is an arylene radical having formula (V), (VI) or (VII) above wherein each ester oxygen atom of fluorophosphite (I) is bonded to a ring carbon atom of $A^1$ and $A^2$;
X is (i) a chemical bond directly between ring carbon atoms of $A^1$ and $A^2$; or (ii) an oxygen atom, a group having the formula —$(CH_2)_y$— wherein y is 2 to 4 or a group having the formula

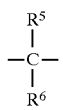

wherein $R^5$ is hydrogen, alkyl or aryl; $R^6$ is hydrogen or alkyl; and the group —$C(R^5)(R^6)$— contains up to about 8 carbon atoms; and
wherein $R^3$ and $R^4$ are independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of such alkyl, alkoxy, alkanoyl, alkoxycarbonyl and alkanoyloxy groups contains up to about 8 carbon atoms; p and q each is 0, 1 or 2.

12. The catalyst solution according to claim 11 wherein the ratio of gram moles fluorophosphite ligand to gram atoms rhodium is about 1:1 to 50:1 and the hydroformylation solvent is selected from alkanes, cycloalkanes, alkenes, cycloalkenes, carbocyclic aromatic compounds, esters, ketones, acetals and ethers which are liquid at the pressure at which the process is being operated.

13. A process for preparing an aldehyde which comprises contacting an olefin, hydrogen and carbon monoxide with a solution of a catalyst composition comprising rhodium; one or more fluorophosphite compounds having the general formula

wherein $R^1$ and $R^2$ are hydrocarbyl radicals which contain a total of up to about 40 carbon atoms;
and a hydroformylation solvent;
wherein the ratio of gram moles fluorophosphite ligand to gram atoms rhodium is at least 1:1.

14. The process according to claim 13 wherein the concentration of rhodium in the solution is in the range of about 20 to 300 mg per liter and the process is carried out at a temperature of about 50° to 135° C. at a pressure in the range of ambient to about 36 bars absolute.

15. The process according to claim 14 wherein the concentration of rhodium in the solution is in the range of about 20 to 300 mg per liter; the process is carried out at a temperature of about 50° to 135° C. at a pressure in the range of ambient to about 36 bars absolute; and the fluorophosphite compounds have the general formula

wherein $R^1$ and $R^2$ individually are independently selected from alkyl of up to about 8 carbon atoms, benzyl, cyclopentyl, cyclohexyl, cycloheptyl or an aryl group having the formula:

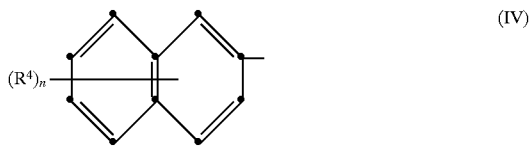

wherein $R^3$ and $R^4$ are independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of such alkyl, alkoxy, alkanoyl, alkoxycarbonyl and alkanoyloxy groups contains up to about 8 carbon atoms; m and n each is 0, 1 or 2; and the total carbon atom content of the hydrocarbyl radicals represented by $R^1$ and $R^2$ is about 2 to 35 and wherein the ratio of gram moles fluorophosphite ligand to gram atoms rhodium is about 1:1 to 70:1.

16. The process according to claim 13 wherein the olefin is a mono-α-olefin of 2 to 10 carbon atoms.

17. The process according to claim 15 wherein the olefin is a mono-α-olefin of 2 to 10 carbon atoms.

18. The process according to claim 14 wherein the concentration of rhodium in the solution is in the range of about 20 to 300 mg per liter; the process is carried out at a temperature of about 50° to 135° C. at a pressure in the range of ambient to about 36 bars absolute; and the fluorophosphite compound has the general formula

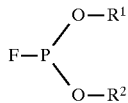 (I)

wherein $R^1$ and $R^2$ collectively represent a divalent hydrocarbylene group containing about 12 to 36 carbon atoms.

19. The process according to claim 18 wherein the ratio of gram moles fluorophosphite ligand to gram atoms rhodium is about 1:1 to 70:1 and $R^1$ and $R^2$ collectively represent alkylene of about 2 to 12 carbon atoms, cyclohexylene, an arylene group having the formula

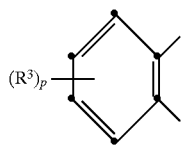 (V)

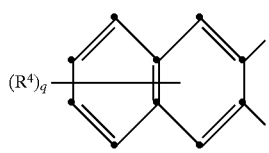 (VI)

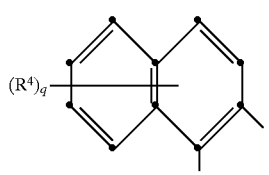 (VII)

or a radical having the formula

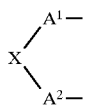

wherein
each of $A^1$ and $A^2$ is an arylene radical having formula (V), (VI) or (VII) above wherein each ester oxygen atom of fluorophosphite (I) is bonded to a ring carbon atom of $A^1$ and $A^2$;
X is (i) a chemical bond directly between ring carbon atoms of $A^1$ and $A^2$; or (ii) an oxygen atom, a group having the formula —$(CH_2)_y$— wherein y is 2 to 4 or a group having the formula

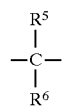

wherein $R^5$ is hydrogen, alkyl or aryl; $R^6$ is hydrogen or alkyl; and the group —$C(R^5)(R^6)$— contains up to about 8 carbon atoms; and wherein $R^3$ and $R^4$ are independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of such alkyl, alkoxy, alkanoyl, alkoxycarbonyl and alkanoyloxy groups contains up to about 8 carbon atoms; p and q each is 0, 1 or 2.

20. The process according to claim 19 wherein fluorophosphite compound has the formula

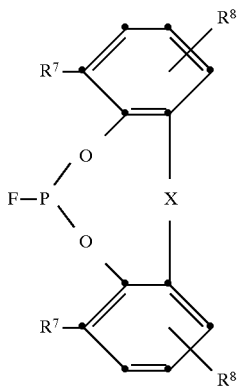

wherein each $R^7$ is alkyl of 3 to 8 carbon atoms; each $R^8$ is hydrogen, alkyl of 1 to 8 carbon atoms or alkoxy of 1 to 8 carbon atoms; and X is (i) a chemical bond directly between ring carbon atoms of each phenylene group to which X is bonded; or (ii) a group having the formula

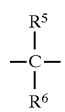

wherein each of $R^5$ and $R^6$ is hydrogen or alkyl of 1 to 8 carbon atoms; and the olefin is a mono-α-olefin of 2 to 10 carbon atoms.

21. A process for preparing an aldehyde which comprises contacting an olefin, hydrogen and carbon monoxide with a solution of a catalyst composition comprising rhodium, a fluorophosphite compound of the formula

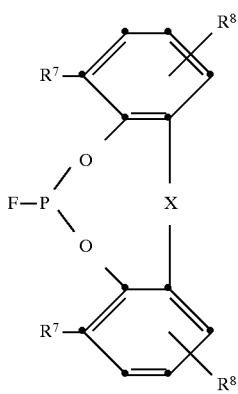

wherein each $R^7$ is alkyl of 3 to 8 carbon atoms; each $R^8$ is hydrogen, alkyl of 1 to 8 carbon atoms or alkoxy of 1 to 8 carbon atoms; and X is a group having the formula

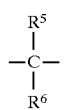

wherein each of $R^5$ and $R^6$ is hydrogen or alkyl of 1 to 8 carbon atoms; and the olefin is a mono-α-olefin of 3 to 8 carbon atoms; and where the ratio of gram moles of fluorophosphite ligand to gram atoms rhodium is at least 1:1; and the process is carried out at a temperature of 50° to 135° C. and the normal to iso ratio of the aldehyde product is controlled by varying the partial pressure of carbon monoxide in the reactor gas between the 3.0 and 8.0 bars absolute.

* * * * *